US006555688B1

(12) United States Patent
Klockemann et al.

(10) Patent No.: US 6,555,688 B1
(45) Date of Patent: Apr. 29, 2003

(54) METHOD FOR THE PRODUCTION OF TRIETHYLENE DIAMINE MAKING USE OF ETHYLENE DIAMINE

(75) Inventors: Werner Klockemann, Buchholz (DE); Erich Frauendorfer, Emden (DE); Matthias Frauenkron, Freinsheim (DE); Bernd Stein, Seeheim-Jugenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/609,740

(22) Filed: Jul. 5, 2000

(30) Foreign Application Priority Data

Jul. 5, 1999 (DE) .......................... 199 30 736

(51) Int. Cl.[7] ............................................. C07D 487/08
(52) U.S. Cl. ...................................................... 544/352
(58) Field of Search ......................................... 544/352

(56) References Cited

U.S. PATENT DOCUMENTS

| 2,937,176 A | 5/1960 | Herrick et al. | |
| 3,285,920 A | 11/1966 | Muhibauer et al. | |
| 3,702,886 A | 11/1972 | Argauer et al. | 423/328 |
| 3,956,329 A | 5/1976 | Murakami et al. | |
| 4,289,881 A | 9/1981 | Imre et al. | |
| 4,804,758 A | 2/1989 | Hoelderich et al. | 544/352 |
| 4,966,969 A | 10/1990 | Sato et al. | |
| 4,973,709 A | 11/1990 | Olson et al. | 548/954 |
| 5,041,548 A | 8/1991 | Sato et al. | |
| 5,731,449 A | 3/1998 | Li et al. | |
| 5,741,906 A | 4/1998 | Santiesteban et al. | |
| 5,756,741 A | 5/1998 | Armor et al. | |
| 6,084,096 A * | 7/2000 | Li et al. | 544/352 |
| 6,350,874 B1 * | 2/2002 | Ogawa | 544/352 |

FOREIGN PATENT DOCUMENTS

| DE | 206896 | 2/1984 |
| DE | 3735212 | 4/1989 |
| DE | 3934459 A1 * | 4/1991 |
| EP | 0158319 | 10/1985 |
| EP | 312734 | 4/1989 |
| EP | 0 349 859 | 1/1990 |
| EP | 0382 055 | 8/1990 |
| EP | 0 423 526 | 4/1991 |
| EP | 0952152 | 10/1999 |
| EP | 1 041 073 | 10/2000 |
| RU | 2071475 | 1/1997 |
| RU | 2114849 | 7/1998 |
| WO | WO98/55228 | 12/1988 |

OTHER PUBLICATIONS

Ullmann's Encyclopedia of Industrial Chemistry Fifth Ed. vol. A28 (1996) pp. 487–502.
Weitkamp et al., *Catalysis and Zeolites, Fundamentals and Applications*, Chapter 3 pp. 81–197, 1999.
Frauenkron et al., U.S. application Ser. No. 09/765,625 filed on Jun. 26, 2001.
Reichle "Reactions of Aliphatic α–ω–Diamines in H[+]–Pentasils" Journal of Catalysts vol. 144 (1993) pp. 556–568.

* cited by examiner

*Primary Examiner*—Mukund J. Shah
*Assistant Examiner*—Thomas C McKenzie
(74) *Attorney, Agent, or Firm*—Keil & Weinkauf

(57) ABSTRACT

The invention in question is concerned with a method for the production of triethylene diamine using ethylene diamine as an educt and zeolite catalysts of the Pentasil type.

14 Claims, No Drawings

METHOD FOR THE PRODUCTION OF TRIETHYLENE DIAMINE MAKING USE OF ETHYLENE DIAMINE

The object of the invention is a method for production of triethylene diamine (1,4-diazabicyclo [2.2.2]octane, hereinafter called TEDA) with use of ethylene diamine (1,2-Diaminoethan, hereinafter called EDPA) and zeolite catalysts of the Pentasil type.

Triethylene diamine is an important base material, being used, inter alia, in the production of pharmaceutics and plastics, in particular as a catalyst in the production of polyurethanes.

The known methods for the production of TEDA basically differ by the nature of the initial products and the catalysts. As a matter of principle, it is beneficial to use favourable base chemicals such as ethanolamine or ethylene diamine (EDA) as educts. Conventional methods have however proven to be not very selective, in particular toward the educt EDA. In addition, a separation of the contaminations resulting from the cycling reaction is difficult, with the result that this method was not able to assert itself technically.

Methods for the production of TEDA using EDA have already been suggested.

The method described in U.S. Pat. No. 3,285,920 (H. G. Muhlbauer et al., Jefferson Chemical Co.) for simultaneous production of TEDA and piperazin (hereinafter called PIP) is a 2-step process, according to which one firstly converts ethylene diamine, ethanolamine and/or their oligomers in the presence of ammonia, hydrogen to a mixture of piperazin and N-(beta-aminoethyl)-piperazin in a reductive amination process making use of metal-oxidic hydrogenating catalysts and then cycles the residue—after separating the piperazin—in the presence of cycling catalysts such as phosphate salts and alumo-silicates. The amounts of TEDA gained are about 25%, those of piperazin about 12%.

In EP 0 158 319 (Union Carbide Corp.), zeolitic catalysts such as ZSM-5 are suggested for the production of TEDA. Basically, EP 0 158 319 has cyclic amine compounds as educts as its object.

From DE 37 35 212-A1 (corresponds to EP 0 313 753) and DE 37 35 214-A1 (corresponds to EP 0 313 734, both Huils AG) a method for production of a PIP/TEDA mixture by conversion of ethanolamines and/or ethylene diamine in the presence of a zeolite of the Pentasil type is known. According to this method, the chemicals are guided to a reaction at 280 to 380° C., an LHSV (liquid hourly space velocity) of 0.1 to 10 h$^{-1}$ and at an absolute pressure of 0.1 to 10 bar in a gaseous form via a packetbed catalyst. It is also suggested that the initial compounds be used together with a diluting agent, e.g. water.

According to EP 0 382 055-A1 (corresponds to DE 39 036 22, BASF AG) 1,2-diaminoethane and 0 to 200 mol% piperazin are converted to TEDA on aluminium, boron, gallium and/or iron silicate zeolites at the following preferred reaction conditions in the case of a liquid phase reaction: reaction temperature 100 to 300° C., pressure 1 to 5 bar and WHSV 1 to 10 h$^{-1}$. If the reaction is conducted in the gaseous phase, temperatures of 200 to 400° C. are preferred. A solvent or diluting agent such as water can be used.

DE 39 34 459-A1 (Bayer AG) describes a method for the production of TEDA and piperazin (PIP) by conversion of EDA on zeolites of the Pentasil type with weakened acidity. According to DE 39 34 459-A1, such zeolites are available by replacement of at least 50% of all the replaceable cations with alkali metal cations or are zeolites in which the aluminium of the zeolite framework has been replaced isomorphally by iron. ZSM-5 catalysts not treated with this method have proven to be less suitable according to DE 39 34 459-A1. The conversion is conducted at a temperature of 300 to 400° C. and with a catalyst load of 0.03 to 2.0 kg/kg EDA/kg zeolite/h, with EDA/water mixtures with 2 to 25 Mol, preferably 5 to 15 Mol, water per Mol EDA being used.

In newer U.S. patent literature (U.S. Pat. No. 5,731,449 and U.S. Pat. No. 5,741,906; Air Products and Chemicals Inc. and U.S. Pat. No. 5,041,548 Idemitsu Kosan Ltd.) methods for the production of TEDA from EDA making use of modified Pentasil catalysts are suggested. According to U.S. Pat. No. 5,041,548 (Idemitsu Kosan Ltd.) there is, for example, the suggestion of using zeolite catalysts of the ZSM-5 type produced in the presence of organic cycling agents such as tetraalkyl ammonium compounds.

In U.S. Pat. No. 5,756,741 (Air Products and Chemicals Inc.), a two-phased method is described, in which an interim phase rich with piperazin is firstly produced from an aminocompound through cyclization reaction, this then being converted to TEDA by adding, for example, EDA.

The methods according to the state of the art have a low selectivity with regard to the formation of TEDA, a large amount of water as a diluting agent and, if applicable, an additional extensive catalyst production/modification in common. The objective of the invention is to develop a method for the production of TEDA from easily accessible initial compounds containing N which is simple to execute and above all is to guarantee an increased selectivity compared with the state of the art. The object of the invention is thus a method for the conversion of ethylene diamine (EDA) making use of zeolite catalysts which avoids the disadvantages of the state of the art, in particular low selectivity and a large production of piperazin, and leads to large yields of high-purity TEDA.

The object is achieved according to the invention by a method for production of triethylene diamine from ethylene diamine making use of zeolite catalysts, wherein the educt flow in continuous operation contains 5 to 80% by weight of ethylene diamine, preferably 20 to 70% by weight and particularly preferably 35 to 60% by weight, the zeolite catalysts are zeolite catalysts of the Pentasil type with Si: Al atom ratios of 100:1 to 700:1, preferably 100:1 to 350:1, particularly preferably 100:1 to 250:1 and in particular from 150:1 to 250:1, and exist or are used at least partly in the H+ and/or NH$_4$+ form, preferably in the H+ form, the educt flow has a water content of 2 to 60% by weight, preferably 10 to 40% by weight, particularly preferably 10 to 30% by weight, relative to the educt flow and the reaction temperature is between 290 and 400° C., preferably 310 and 370° C., particularly preferably 310 and 350° C.

Preferred embodiments of the invention are the objects of the sub-claims.

The zeolite catalyst of the Pentasil type used as a catalyst in the method in the invention for the production of triethylene diamine has a crystalline skeleton structure of silicone dioxide and aluminium dioxide. To the extent that the zeolite catalyst of the Pentasil type has the Si:Al atom ratio as stated above, there are essentially no additional requirements either with regard to the zeolite material as such or with regard to the method according to which this can be obtained.

For example, the following types of zeolite catalysts of the Pentasil type are suitable for use in the invention in question: ZSM-5, ZSM-11, ZSM-23, ZSM-53, NU-87, ZSM-35, ZSM-48 and mixed structures of at least two of the above mentioned zeolites, in particular ZSM-5 and ZSM-11 as well as their mixed structures.

If the zeolite catalyst of the Pentasil type according to the invention is not available in the required acid H form due to the kind of production, but, for example, in the Na form (or any other salt form), then it can be completely or partially transferred into the required H+ or $NH_4+$ form by an exchange of ions, e.g. with ammonium ions with subsequent calcination or by treatment with acids. In order to achieve the highest possible selectivity, high turnovers and long service lives, it can be a benefit if the zeolites are modified. A suitable modification of the catalysts comprises the zeolitic material—deformed or undeformed—being subjected to a treatment according to the state of the art with protonic acids—such as hydrochloric acid, sulphuric acid, hydrofluoric acid, phosphoric acid, a carbonic acid or dicarbonic acid and/or complex-formers and/or water vapour.

Further, the following reaction conditions have proven to be favourable:

a WHSV (weight hourly space velocity) from 0.05 to 6 $h^{-1}$, preferably from 0.2 to 1 $h^{-1}$, particularly preferably from 0.6 to 1 $h^{-1}$ and a pressure (absolute) from 0.1 to 10 bar, preferably from 0.8 to 2 bar.

The educt flow can be enriched with an inert carrier gas such as nitrogen and/or ammonia and is preferably saturated with ammonia for this purpose.

Preferably, the reaction is guided in such a way that water, EDA and PIP in a weight ratio of 10 to 40:20 to 60:20 to 50, preferably of 10 to 40:20 to 50:20 to 50, particularly preferably of 15 to 25:20 to 50:20 to 50, in particular e.g. 20:40:40 are added during continuous operation in a steady state, whereby the share of the PIP or the EDA can, if necessary, be lowered or raised in favour of one or to the detriment of the other, respectively. It is also possible to include other amino-compounds in the reactor and to convert them to TEDA. Such amino-compounds are preferably piperazin derivatives such as hydroxyethyl piperazin or aminoethyl piperazin. Adding these compounds to the educt flow should preferably not exceed a share of 20% by weight. 1,2-ethanolamine can also be used. But as this can lead to the formation of side-products difficult to separate out, it is preferred if less than 5% by weight of ethanolamine is used.

It has been seen that with an addition of in particular 35 to 60% by weight, e.g. 40% by weight, of EDA, the reaction can be conducted continuously in steady-state in such a way that EDA almost completely converts to TEDA and PIP, with PIP being removed from the product flow, e.g. by distillation, with optionally any other interim and/or side-products which may exist and mixed with about the same amount of EDA (in % by weight), again can be added to the reaction.

The method is preferably carried out by setting a corresponding EDA/PIP ratio in the reactor feed in such a way that the consumption of PIP tends towards 0 in the balance, i.e. as a result, basically no additional PIP is added during the continuous operation.

With such a conduction of the reaction, it was surprisingly seen that the amount of EDA discharged is practically zero. The separation of the discharge from the reactor is particularly simple in accordance with the method according to the invention.

A particular advantage of the method is that interim fractions containing both TEDA as well as piperazin can be fed to the catalyst again. Further, automatic waste products of other amino-compounds from other amino-cyclization/condensation reactions can be added to the reaction according to the invention without the yields considerably deteriorating.

Thus, the following advantages are achieved with the method according to the invention:

The method permits replacement of the EDA used as an educt by piperazin or piperazin derivatives such as hydroxyethyl piperazin or aminoethyl piperazin, depending upon price and availability.

High selectivity relative to the conversion of EDA to TEDA is achieved.

The basically sole side-product, piperazin, can be added to the process again with correct reaction engineering and converted to TEDA. Mixtures of non-converted piperazin and TEDA can also be added to the catalyst again, as it has been seen that TEDA is stable under the reaction conditions.

To increase the stability, the zeolites to be used according to the invention can be based, e.g. on cellulose materials, clays, binding agents or metal oxides such as alumina, aluminium oxide, silicone oxide. Further, it is possible to use them as granulates, in a spherical form or applied to glass or other bodies.

In principle, all methods for achieving a corresponding shaping can be used as strengthening shaping processes for the zeolites to be used according to the invention. Preferable methods are those in which the shaping is achieved by extrusion in customary extruders, for example in strands with a diameter of customarily 1 to 10 mm, in particular 2 to 5 mm. If binding agents and/or ancillaries are needed, the extrusion is sensibly preceded by a mixing or kneading process. If necessary, a calcination step can be carried out after the extrusion. The strands obtained are made smaller if so required, preferably as granulate or split with a particle diameter of 0.5 to 5 mm, in particular 0.5 to 2 mm. This granulate or split and also catalyst bodies formed in any other way contain practically no finer-grained particles than those with a 0.5 mm minimum particle diameter.

In a preferred embodiment, the shaped zeolite to be used according to the invention has up to 80% by weight binding agent relative to the overall mass of the catalyst. Particularly preferred contents of binding agents are 1 to 50% by weight, in particular 3 to 35% by weight. In principle, the binding agents can be any compounds used for such purposes, compounds, in particular oxides, of silicone, aluminium, boron, phosphor, zirconium and/or titanium being preferred. Silicone dioxide is of special interest as a binding agent, whereby $Sio_2$ can also be added to the shaping process as siliceous sol or in the form of tetra-alkoxysilanes. Oxides of magnesium and beryllium and clays, e.g. montmorillonite, kaolin, bentonite, halloysite, dickite, nacrite and anauxite can also be used as binding agents.

Examples of auxiliaries for the strengthening shaping process are stranding ancillaries for the extrusion, a customary stranding agent being methyl cellulose. As a rule, such agents are completely combusted in a subsequent calcination step.

When using the zeolite catalyst to be used according to the invention, it can be regenerated after a deactivation, regardless of its shape, through a method in which the regeneration is done by purposeful combustion of the coatings responsible for the deactivation. Work will preferably be done in an inert gas atmosphere containing precisely defined amounts of substances providing oxygen. Such a regeneration procedure is described inter alia in WO 98/55228 and DE 19723949-A1, the disclosure of which is hereby incorporated in the present application to the complete extent by reference.

The zeolite catalyst to be used according to the invention and to be regenerated is heated to a temperature in the range from approximately 250° C. to 800° C., preferably approximately 400° C. to 550° C. and in particular approximately 450° C. to 500° C., either in the conversion device or in an external furnace in an atmosphere containing 0.1 to approximately 20 volume parts of substances providing oxygen, particularly preferably oxygen. The heating is preferably done at a heating rate of approximately 0.1° C./min. to approximately 20° C./min., preferably approximately 0.3° C./min to approximately 15° C./min. and in particular 0.5° C./min. to 10° C./min.

During this heating-up phase, the catalyst is heated up to a temperature at which the coatings on it, mostly organic, begin to decompose, whereas the temperature is silo multaneously regulated by the oxygen content and thus does not rise to an extent causing damage to the catalyst structure. The slow increase of the temperature and remaining at a low temperature by setting the corresponding oxygen contents and the corresponding heating output is an essential step towards preventing a local overheating of the catalyst with high organic loads on the catalyst to be regenerated.

If the temperature of the exhaust air flow at the discharge of the reactor drops despite increased amounts of substances supplying oxygen in the gas flow, the burn-off of the organic coatings is over. The duration of the treatment is generally approximately 1 to 30, preferably approximately 2 to approximately 20 and in particular approximately 3 to approximately 10 hours.

In the subsequent cooling of the catalyst regenerated in this way, it should be ensured that the cooling is not done too quickly ("quenching"), as otherwise the mechanical strength of the catalyst can be negatively influenced.

The term "substances supplying oxygen" used above covers all substances which are in a position to pass on oxygen or to remove waste products containing carbon and/or nitrogen under the prevailing regeneration conditions. The following are particularly to be mentioned: nitrous oxides with the formula $N_xO_y$, with x and y being selected in such a way that a neutral nitrous oxide results, $N_2O$, exhaust gas flow from an adipinic acid plant containing $N_2O$, NO, $NO_4$, ozone or a mixture of two or more of them. If $CO_2$ is used as a substance supplying oxygen, temperatures of 500° C. to 800° C. are preferably set during the regeneration.

In a further embodiment of the method according to the invention, the catalyst which has at least been partly deactivated is washed before heating according to the regeneration procedure with a solvent in the conversion reactor or in an external reactor in order to remove valuable product still adhering to it. The washing is done in such a way that the valuable products adhering to the catalyst can be removed from the latter, but temperature and pressure are not selected so high that most organic coatings are also removed. Preferably, the catalyst is merely rinsed with a suitable solvent. In this way, all solvents in which the given conversion product dissolves well can be considered for this washing procedure. The amount of solvent used and the duration of the washing process are not critical. The washing process can be repeated a number of times and carried out at a higher temperature. If $CO_2$ is used as a solvent, over-critical pressure is preferred, otherwise the washing procedure can be carried out under standard pressure or increased or over-critical pressure. After the end of the washing process, the catalyst is generally dried. Although the drying process is uncritical in general, the drying temperature ought not to exceed the boiling temperature of the solvent used for the washing, in order to avoid a sudden evaporation of the solvent in the pores, in particular in the micropores, as this can also lead to damage to the catalyst.

A preferred embodiment of the production process can comprise the continuous method for synthesis of TEDA according to the invention not having to be interrupted in the regeneration of the catalyst according to the invention in order to increase the process throughput. This can be achieved by making use of at least two reactors switched in parallel.

The catalyst regeneration can be conducted in such a way that at least one of the reactors switched in parallel is separated from the reaction phase in question and the catalyst contained in this reactor is regenerated, with at least one reactor always being available in the course of the continuous method for the conversion of EDA.

If necessary, not only water, but also other diluting agents such as nitrogen or ammoniac (e.g. over and above the saturation of the educt flow) can be added to the catalyst. It is a benefit if the educt components are pre-heated.

The processing of the reaction mixture can be done by customary methods. A particularly purposeful form comprises starting the reaction mixture and separating by distillation. If required, TEDA can be recrystallised from suitable solvents in order to improve its purity. However, this is normally not necessary as TEDA can be produced with purities of greater than 95% by weight with the method according to the invention.

EXPERIMENTAL EXAMPLE

In a packet-bed reactor (1 cm inner diameter, 1 m length), the reaction was carried out under isothermal conditions at 320° C. for more than 24 h. The reaction products were separated by customary methods and characterised. The quantitative determination of the reaction products was done by gas chromatography.

A ZSM-5 zeolite was used as a catalyst ($SiO_2/Al_2O_3$ molar ratio of 400 corresponding to an Si:Al atom ratio of 200, H+ form), which was washed with 5% HCl before stranding with 20% by weight $SiO_2$ (relative to the overall mass of the finished strands).

The initial product comprised 16% water, 36% ethylene diamine, 36% piperazin and 12% triethylene diamine. The educt flow is set in such a way that a catalyst load (WHSV, weight hourly space velocity, g educt mixture/g catalyst/h ) of 0.6 h to 1 h resulted. The turnover of ethylene diamine was 100% and the yield of triethylene diamine 97.5%.

The product and educt mixture had roughly the following compositions (each in % by weight) in exemplary preparations done in approximately a stationary state, Educt mixture
 $H_2O$ 15, EDA 36; PIP 36,0; TEDA 12; side-products 1
Product mixture
 $H_2O$ 17, EDA -; PIP 41; TEDA 38; side-products 3
The following compounds were detected as side-products/interim products:
 dimethyl-pyrazine 0.4; N-ethyl-piperazin 0.4; DETA 0.2 NAEP 1.0; higher oligomers of EPI (Sdp. >200° C.) 1.3.

What is claimed is:

1. A method for the production of triethylene diamine from ethylene diamine with use of zeolite catalysts, wherein the educt flow in continuous operation contains 5 to 80% by weight of ethylene diamine, the zeolite catalysts are zeolite catalysts of the Pentasil type with Si:Al atom ratios of 150:1 to 700:1, and are present or are used at least partially in the H+ and/or $NH_4$+ form, the educt flow comprises water in a content of 2 to 60% by weight and the reaction temperature is between 290 and 400° C.

2. The method according to claim 1, wherein the zeolite catalysts have Si:Al atom ratios of 150:1 to 250:1.

3. The method according to claim 1, wherein the reaction temperature is between 310 and 370° C.

4. The method according to claim 1, wherein the educt flow in continuous operation contains 20 to 70% by weight of ethylene diamine.

5. The method according to claim 1, wherein the WHSV is between 0.05 and 6 h$^{-1}$.

6. The method according to claim 1, wherein the pressure (absolute) in the reactor is between 0.1 and 10 bar.

7. The method according to claim 1, wherein ethylene diamine is used together with 0 to 200 Mol% piperazin.

8. The method according to claim 1, wherein water/ethylene diamine/piperazin are used in the educt flow in an approximate weight ratio of 10 to 40:20 to 50:20 to 50.

9. The method according to claim 1, wherein the zeolite catalysts of the Pentasil type are zeolites of the type ZSM-5, ZSM-11 or mixed structures thereof.

10. The method according to claim 1, wherein at least partially zeolite catalysts are used which are regenerated in an inert gas atmosphere in the presence of oxygen or substances supplying oxygen at a temperature in the range of 250° C. to 800° C.

11. The method according to claim 1, wherein the conversion is done continuously without interruption in at least two reaction areas switched in parallel, at least one of which can be separated from the educt and/or product flow for the regeneration of the catalyst.

12. The method according to claim 1, wherein the zeolite catalysts of the Pentasil type are washed with a protonic acid before use in the method.

13. The method according to claim 10, wherein the zeolite catalysts are regenerated with a heating rate of about 0.1° C./min. to about 20° C./min.

14. The method according to claim 1, wherein the zeolite catalysts of the Pentasil type are washed with a protonic acid before application to a carrier and/or stranding before use in the method.

* * * * *